United States Patent [19]

Spiske et al.

[11] Patent Number: 5,248,427
[45] Date of Patent: Sep. 28, 1993

[54] REMOVAL OF WATER FROM MIXTURES WITH ALCOHOLS AND/OR CARBOXYLIC ACIDS AND/OR CARBOXYLIC ESTERS

[75] Inventors: Luise Spiske, Im Hahnboehl; Harald Meissner, Bad Doerkheim; Werner Hefner, Lampertheim; Andreas Huebner, Unna; Hermann Steinhauser, Cologne; Guido Ellinghorst, Overath, all of Fed. Rep. of Germany

[73] Assignee: BASF Aktiengesellschaft, Ludwigshafen, Fed. Rep. of Germany

[21] Appl. No.: 905,188

[22] Filed: Jun. 26, 1992

Related U.S. Application Data

[63] Continuation of Ser. No. 757,369, Sep. 10, 1991, abandoned.

[30] Foreign Application Priority Data

Sep. 15, 1990 [DE] Fed. Rep. of Germany ....... 4029349

[51] Int. Cl.$^5$ .............................................. B01D 15/00
[52] U.S. Cl. .................................. 210/640; 210/651; 210/490
[58] Field of Search ............... 210/640, 490, 500.23, 210/500.27, 500.37; 55/16, 158; 427/40; 264/22

[56] References Cited

U.S. PATENT DOCUMENTS

| 2,981,680 | 4/1961 | Binning | 210/640 |
|---|---|---|---|
| 3,182,043 | 4/1965 | Kirkland | 210/640 |
| 3,657,113 | 4/1972 | Stancell et al. | 210/490 |
| 4,032,440 | 6/1977 | Yasuda | 210/500.33 |
| 4,230,463 | 10/1980 | Henis et al. | 55/16 |
| 4,347,139 | 8/1982 | Hayashi | 210/500.37 |
| 4,533,369 | 8/1985 | Okita | 55/158 |
| 4,635,585 | 1/1987 | Conrad et al. | 118/316 |
| 4,692,347 | 9/1987 | Yasuda | 427/40 |
| 4,755,299 | 7/1988 | Brüschke | 210/640 |
| 4,769,140 | 9/1988 | van Dijk et al. | 210/184 |
| 4,784,769 | 11/1988 | Giordano, Jr. et al. | 210/550.27 |
| 4,806,246 | 2/1989 | Nomura | 210/500.23 |
| 4,832,713 | 5/1989 | Yamada et al. | 210/490 |
| 4,960,519 | 10/1990 | Pasternak et al. | 55/16 |
| 4,961,855 | 10/1990 | Reale, Jr. et al. | 55/16 |
| 4,963,165 | 10/1990 | Blume et al. | 55/16 |
| 4,971,699 | 11/1990 | Bartels | 55/16 |
| 4,976,856 | 12/1990 | Van Der Scheer et al. | 210/490 |
| 5,049,167 | 9/1991 | Castro et al. | 55/16 |
| 5,151,190 | 9/1992 | Seiryo | 210/640 |

OTHER PUBLICATIONS

Suhr, Houben-Weyl 415b, 1559-1591.
J. Macromolecular Science Chem. A 10 (1976), 367-368 (3).

*Primary Examiner*—Robert A. Dawson
*Assistant Examiner*—Ana M. Fortuna
*Attorney, Agent, or Firm*—Keil & Weinkauf

[57] ABSTRACT

In a process for removing water by pervaporation or vapor permeation from mixtures with alcohols and/or carboxylic acids and/or carboxylic esters by bringing the mixture into contact with one side of a membrane and removing the water-containing permeate in vapor form from the other side of the membrane, the membrane used has been obtained by plasma polymerization.

9 Claims, 1 Drawing Sheet

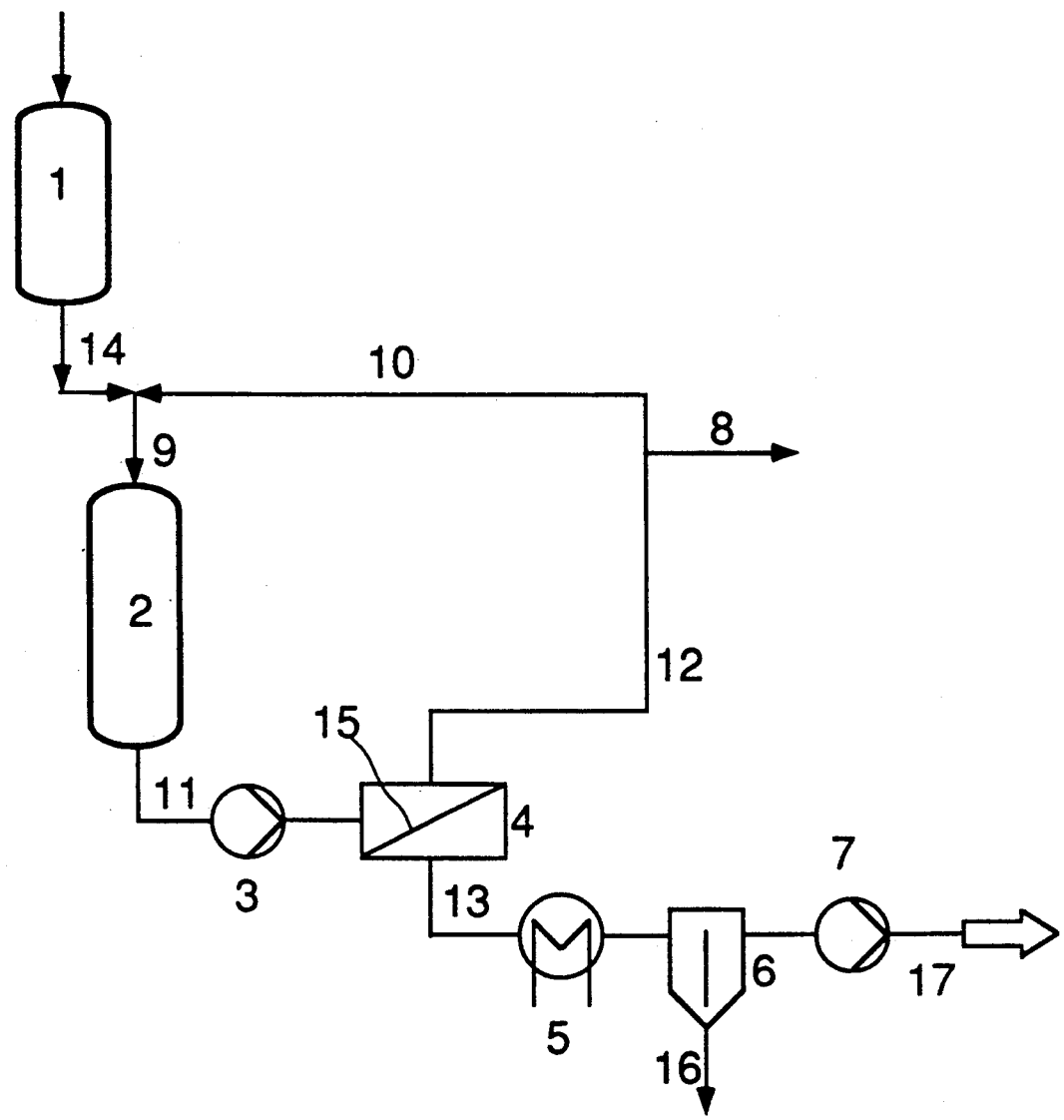

REMOVAL OF WATER FROM MIXTURES WITH ALCOHOLS AND/OR CARBOXYLIC ACIDS AND/OR CARBOXYLIC ESTERS

This application is a continuation application of Ser. No. 07/757,369, filed Sep. 10, 1991 and now abandoned.

The present invention relates to a process for removing water from a mixture with alcohols and/or carboxylic acids and/or carboxylic esters, for example a reaction mixture from carboxylic ester production, by pervaporation or vapor permeation.

EP-Al-0 210 055 discloses a process for preparing liquid esters by reacting an alcohol with a carboxylic acid in the presence of an acidic catalyst, wherein the water of reaction is continuously removed from the reaction mixture by pervaporation through a membrane. However, the membranes used in said process do not have satisfactory permeability and selectivity for water. Yet a very high selectivity of the membrane for water is necessary to minimize the apparatus requirements and energy consumption for the vaporization and condensation in the pervaporation part of a plant and the level of organics in the removed water. High membrane permeabilities are required to minimize the required membrane area, membrane area being a significant cost factor in equipping and maintaining a membrane separation plant.

It is an object of the present invention to devise a process for removing water from mixtures of water and alcohols and/or carboxylic acids and/or carboxylic esters which is free or substantially free of the disadvantages of existing processes.

We have found that this object is achieved by an advantageous process for removing water from a mixture of water and an alcohol, a carboxylic acid or a carboxylic ester by pervaporation or vapor permeation by bringing the mixture into contact with one side of a membrane and removing the water-containing permeate in vapor form from the other side of the membrane, which comprises using a membrane obtained by plasma polymerization.

The novel process makes it possible to remove water from a mixture with alcohols and/or carboxylic acids and/or carboxylic esters, in particular the water of reaction from a reaction mixture obtained in the preparation of carboxylic esters in the presence of acidic catalysts, in an advantageous and economical manner because of the high water selectivity and permeability of the membrane used and its heat, acid and solvent resistance.

The process of the present invention is used with particular advantage for removing the water of reaction from the reaction mixture obtained in the preparation of carboxylic esters by reaction of alcohols with carboxylic acids in the presence of acidic catalysts.

Suitable alcohols for preparing carboxylic esters are in general monohydric or dihydric, preferably monohydric aliphatic alcohols of from 1 to 12 carbon atoms, preferably from 1 to 10 carbon atoms, in particular from 1 to 8 carbon atoms. Suitable alcohols are for example methanol, ethanol, n-propanol, isopropanol, n-butanol, isobutanol, the pentyl alcohols, the hexyl alcohols, 2-ethylhexyl alcohol, methylglycol, ethylglycol, butylglycol, glycol, diethylene glycol, propylene glycol, 1,4-butanediol and 1,5-pentanediol.

Suitable carboxylic acids for preparing carboxylic esters are in general mono- and dicarboxylic acids, preferably monocarboxylic acids, having from 1 to 10 carbon atoms, preferably from 1 to 6 carbon atoms, in particular from 1 to 4 carbon atoms. Examples are formic acid, acetic acid, propionic acid and butyric acid.

Suitable acidic catalysts for preparing carboxylic esters are in general mineral acids such as sulfuric acid and phosphoric acid, organic sulfonic acids such as benzenesulfonic acid and p-toluenesulfonic acid and preferably ion exchange materials in the hydrogen form, for example sulfonated polystyrene resins such as ring sulfonated crosslinked styrene-divinylbenzene copolymers.

In general, the esterification is conducted at from 20° C. to 150° C., preferably at from 40° C. to 120° C.

Examples of carboxylic esters which are obtained by the process of the present invention are n-propyl acetate, isobutyl acetate, n-pentyl acetate, 2-methyl-1-butyl acetate, 3-methyl-1-butyl acetate, 1,5-pentylene diacetate, 2-ethylhexyl acetate, n-propyl propionate, n-pentyl propionate, 2-methyl-1-butyl propionate, 3-methyl-1-butyl propionate, methylglycol acetate, ethylglycol acetate, butylglycol acetate, butyldiglycol acetate and propylene glycol diacetate.

The removal of water from the mixture with alcohols and/or carboxylic acids and/or carboxylic esters, for example from the reaction mixture of the esterification reaction, is effected by pervaporation or vapor permeation by bringing the mixture into contact with one side of the membrane and removing the water-containing permeate in vapor form from the other side of the membrane.

Suitable apparatus for separating mixtures by the pervaporation or vapor permeation process of the present invention is constructed for example of a crude-mixture compartment for the mixture to be separated; a permeate compartment for the removed permeate; and a membrane arranged inbetween; and is provided with at least one feed channel which communicates with the crude-mixture compartment and at least one exit channel which communicates with the permeate compartment (cf. for example DE-A13 529 175). The crude-mixture compartment advantageously also contains an exit channel for that part of the mixture (retentate) which is retained by the membrane.

The pervaporation or vapor permeation process of the present invention is advantageously conducted in such a way that the concentration of water in the permeate is higher than the concentration of water in the feed mixture and the concentration of the organic components in the permeate are lower than the feed mixture.

The permeate obtained in vapor form on the permeate side of the membrane may be conducted away as such, i.e. in vapor form. However, it can also be advantageous to condense the vaporous permeate and to conduct it away in liquid form.

In what follows, further details of the invention will be explained with reference to an illustrative embodiment of an esterification reaction, the process flow diagram of which is depicted in the Figure.

According to the Figure, the alcohol and the carboxylic acid are premixed in vessel 1, drawn off via line 14, combined with the recycle stream 10 and passed via line 9 into reactor 2. The exit mixture from the reactor, comprising the carboxylic ester formed, the water of reaction and any unconverted alcohol and/or unconverted carboxylic acid, is pumped by pump 3 through the pervaporation apparatus 4 for removing water from the reaction mixture by pervaporation or vapor permeation. In apparatus 4, the reaction mixture is divided at membrane 15 into a permeate 13, which contains the water of reaction, and a retentate 12, which contains the carboxylic ester and any unconverted alcohol or unconverted carboxylic acid. The retentate stream 12 is in turn divided into the carboxylic ester product stream 8 and the recycle stream 10. The vaporous permeate 13 is condensed in the heat exchanger 5 and collected in vessel 6, from which the condensate is withdrawn in liquid form via line 16. Uncondensed constituents of the permeate are discharged by the vacuum pump 7 via line 17.

It is an essential feature of the process of the present invention that the pervaporation or vapor permeation membranes used have been prepared by plasma polymerization (cf. for example H. Suhr, Houben-Weyl 4/5 b, pages 1559–1591; J. Macromolecular Science Chemistry A 10 (1976), 367–368 (3)). The membranes used are preferably composite membranes comprising a dense nonporous layer on a support material, the dense nonporous layer being applied to the support material by plasma polymerization. Layer formation by plasma polymerization is advantageously effected by producing reactive species, advantageously in a vacuum, by the action of a plasma, generally produced by glow discharge, on a working gas and reacting the reactive species with one another and/or with the starting components of the working gas to form dense, highly crosslinked polymer layers on the support material.

The support material used is advantageously a porous support material, preferably an asymmetrical porous support material, i.e. a porous support material which has pores of different average diameters on the front and the back. Suitable support materials are based for example on polyacrylonitrile. Preferably, the porous support material used is an ultrafiltration membrane. It is of particular advantage to use composite membranes comprising a dense nonporous layer formed by plasma polymerization on an asymmetrical porous support material, the side of the asymmetrical porous support material with the smaller pores facing the dense nonporous layer.

The working gas used for the plasma polymerization is in general an organic compound which is gaseous or vaporous under the pressure conditions employed. Suitable organic compounds are for example saturated and unsaturated, substituted or unsubstituted, hydrocarbons in general of from 1 to 18 carbon atoms, preferably of from 1 to 15 carbon atoms, in particular of from 1 to 10 carbon atoms. Examples are aliphatic hydrocarbons such as methane, ethane, propane, butanes, hexanes, ethylene, propylene, butylene, butadiene, acetylene, halocarbons such as chlorocarbons, bromocarbons and fluorocarbons, aromatic hydrocarbons such as benzene, toluene and xylene and ethylbenzene, and monomers such as vinyl chloride and acrylonitrile.

The plasma polymerization is preferably conducted with a gas mixture comprising a gaseous or vaporous organic compound and an inorganic gas. It is of particular advantage to use a gas mixture in which at least one component, preferably the inorganic gas, contains nitrogen. The nitrogen-containing inorganic gas used is in general $N_2$, $NH_3$ or an oxide of nitrogen such as $N_2O$, $NO$, $NO_2$, $N_2O_3$ or $N_2O_5$.

The plasma polymerization is for example conducted by flooding the reactor, advantageously a discharge vessel holding the porous support material, with the polymerizing gas mixture and then igniting the gas mixture with a glow discharge. This glow discharge leads to the deposition of a dense plasma polymer layer on the porous support material. After the plasma polymerization has ended, the membrane is removed from the reactor.

Advantageously, the glow discharge is produced with an alternating frequency. Suitable glow discharges can be produced both at low and high frequency, for example within the alternating current range, within the kHz range, within the MHz range and within the microwave range. In general, the gas flows in the discharge vessel is within the range from 0 to 1000 ml (STP)/min, the electric power requirement is within the range from 0.001 to 5 W/cm$^2$, and the pressure is within the range from $1 \cdot 10^{-6}$ to $1 \cdot 10^3$ mbar, preferably within the range from $1 \cdot 10^{-3}$ to $1 \cdot 10^1$ mbar. In general, the treatment time is from 0.1 s to 120 min, preferably from 1 s to 60 min, in particular from 5 s to 30 min. It can be advantageous to operate the discharge vessel with internal electrodes. It can further be advantageous to bring the porous support material into contact with an electrode. This can also be used for moving the porous support material, for example off a reel, as a belt over the electrode for the continuous coating process.

The membranes obtained according to the present invention are noteworthy for the high permeability and selectivity for water. Even in prolonged operation the membrane material showed virtually no losses in respect of permeability and selectivity.

The Examples which follow illustrate the invention.

A) Preparation of composite pervaporation membranes for water removal during esterification a) General method of preparation The composite pervaporation membranes are prepared using ultrafiltration membranes from GFT mbH, Neunkirchen/Heinitz (Germany), as support material ("UF support membrane"). These membranes are prepared by phase inversion. They have molecular exclusion limits of >5000 daltons and consist of polyacrylonitrile.

The deposition of the nonporous separating layer by plasma polymerization is carried out in a vacuum vessel equipped with two electrodes. One of the two electrodes is connected to a high-frequency high-voltage generator. The second electrode is grounded. To produce the composite membrane, the support material is attached to one of the two electrodes. Then the vessel is evacuated ($p < 1 \cdot 10^{-3}$ mbar) and flooded with the process gas. After the separating layer has been deposited, the vessel is evacuated again and then vented, and the composite membrane obtained is removed from the vessel.

b) Preparation examples

EXAMPLE 1

The general method of preparation is followed with the reactor being flooded with a mixture of ammonia and p-xylene and the $NH_3$ flow being 22 ml (STP)/min and the p-xylene flow 14 ml/min. The pressure in the reactor is 0.4 mbar. The discharge is effected with a power requirement of 150 W and is maintained for 5 minutes.

EXAMPLE 2

The general method of preparation is followed with the reactor being flooded with a mixture of nitrogen and ethylene and the $N_2$ flow being 30 ml (STP)/min and the ethylene flow 50 ml (STP)/min. The pressure in the reactor is 0.4 mbar. The discharge is operated with a power requirement of 100 W and maintained for 6 minutes.

EXAMPLE 3

The general method of preparation is followed with the reactor being flooded with a mixture of ammonia, carbon dioxide and ethylene and the $NH_3$ flow being 25 ml (STP)/min, the $CO_2$ flow 25 ml (STP)/min and the $C_2H_4$ flow 40 ml (STP)/min. The pressure in the reactor is 0.4 mbar. The discharge is operated with a power requirement of 150 W and maintained for 10 minutes.

EXAMPLE 4

The general method of preparation is followed with the reactor being flooded with a mixture of ammonia and ethylene and the $NH_3$ flow being 50 ml (STP)/min and the $C_2H_4$ flow 50 ml (STP)/min. The pressure in the reactor is 0.8 mbar. The discharge is operated with a power requirement of 400 W and maintained for 5 minutes.

B) Removal of water in a pervaporation apparatus from mixtures obtained from reacting n-butanol and acetic acid gave n-butyl acetate.

EXAMPLE 5

On feeding a mixture of 9% by weight of water, 15% by weight of acetic acid, 18% by weight of n-butanol and 58% by weight of n-butyl acetate to a pervaporation apparatus equipped with a composite membrane as described in Example 1, this membrane produces with a total flow of 0.6 kg/m²h a permeate mixture of 98.5% by weight of water and 1.5% by weight of organic constituents.

EXAMPLE 6

On feeding a mixture of 1.5% by weight of water, 5% by weight of acetic acid, 6% by weight of n-butanol and 87.5% by weight of n-butyl acetate to a pervaporation apparatus equipped with a composite membrane as described in Example 1, this membrane produces with a total flow of 0.1 kg/m²h a permeate mixture of 99% by weight of water and 1% by weight of organic constituents.

Examples 5 and 6 show the high water selectivity of the membrane, which from varying compositions of the feed mixture for the pervaporation produces permeated streams which always have a water content of more than 98% by weight, combined with a high water permeability of the membrane.

EXAMPLE 7

Example 6 is repeated, except that the composite membrane used is the membrane produced as described in Example 2, which with a total flow of 0.015 kg/m²h produces a permeate mixture of 83% by weight of water and 17% by weight of organic constituents.

EXAMPLE 8

Example 6 is repeated, except that the composite membrane used is the membrane produced as described in Example 3, which with a total flow of 0.3 kg/m²h produces a permeate mixture of 91% by weight of water and 9% by weight of organic constituents.

EXAMPLE 9

Example 5 is repeated, except that the composite membrane used is the membrane produced as described in Example 4, which with a total flow of 3.5 kg/m²h produces a permeate mixture of 97.5% by weight of water and 2.5% by weight of organic constituents.

EXAMPLE 10

Example 6 is repeated, except that the composite membrane used is the membrane produced as described in Example 4, which with a total flow of 0.7 kg/m²h produces a permeate mixture of 99% by weight of water and 1% by weight of organic constituents.

EXAMPLE 11

The apparatus depicted in the Figure, where the membrane obtained in Example 1 is used as membrane 15 in the pervaporation apparatus 4, n-butyl acetate is prepared by esterification of n-butanol with acetic acid in the presence of an ion exchange material as acidic catalyst. The product stream obtained from the esterification of reactor 2 contains the n-butyl acetate in a concentration of 62% by weight. Selective water removal in the downstream pervaporation stage of apparatus 4 produces a product stream 8 having an ester concentration of 88% by weight.

We claim:

1. A process for removing water from a mixture of water and a carboxylic ester and a member selected from the group consisting of an alcohol, a carboxylic acid and mixtures thereof by pervaporation or vapor permeation which comprises bringing the mixture into contact with one side of a membrane and removing the water-containing permeate in vapor form from the other side of the membrane, the membrane being a membrane obtained by plasma polymerization.

2. A process as claimed in claim 1, wherein the mixture is a reaction mixture from the preparation of a carboxylic ester by reacting an alcohol with a carboxylic acid in the presence of an acidic catalyst and the water removed as permeate is the water of reaction.

3. A process as claimed in claim 2, wherein the acidic catalyst used is a mineral acid.

4. A process as claimed in claim 2, wherein the acidic catalyst used is an ion exchange material.

5. A process as claimed in claim 1, wherein the membrane used for removing the water is a composite membrane comprising a dense nonporous layer and an asymmetrical porous support material, the side of the asymmetrical porous support material facing with the smaller pores toward the dense nonporous layer and the dense nonporous layer having been obtained by plasma polymerization.

6. A process as claimed in claim 1, wherein the plasma polymerization is performed by glow discharge in a gas mixture comprising a gaseous or vaporous organic compound and an inorganic gas.

7. A process as claimed in claim 6, wherein the plasma polymerization is performed in a gas mixture in which at least one component is nitrogen.

8. A process as claimed in claim 7, wherein the gas mixture contains a nitrogen-containing inorganic gas.

9. A process as claimed in claim 8, wherein the nitrogen-containing inorganic gas used is $N_2$, $NH_3$ or an oxide of nitrogen or a mixture of two or more of these gases.

* * * * *